United States Patent [19]

Razzano et al.

[11] 4,177,200
[45] Dec. 4, 1979

[54] SILYL PHOSPHATES AS NEUTRALIZING AGENTS FOR ALKALI METAL HYDROXIDES

[75] Inventors: John S. Razzano, Watervliet; Louis P. Petersen, Latham; Bruce A. Ashby, Schenectady, all of N.Y.

[73] Assignee: General Electric Company, Waterford, N.Y.

[21] Appl. No.: 854,562

[22] Filed: Nov. 25, 1977

[51] Int. Cl.² ............................................... C07F 7/08
[52] U.S. Cl. ........................ 260/448.2 N; 260/448.2 E
[58] Field of Search ............................... 260/448.2 N

[56] References Cited

U.S. PATENT DOCUMENTS

| | | | |
|---|---|---|---|
| 3,385,822 | 5/1968 | Brown | 260/448.2 N X |
| 4,084,951 | 4/1978 | Gregory | 260/448.2 N X |
| 4,089,884 | 5/1978 | Shinohara et al. | 260/448.2 N |

*Primary Examiner*—Paul F. Shaver
*Attorney, Agent, or Firm*—E. Philip Koltos; John L. Young; Philip L. Schlamp

[57] ABSTRACT

A silyl phosphate which is an improved neutralizing agent for alkali metal hydroxides in silicone reactions, comprising the reaction product of a linear siloxane, and a phosphorous oxyhalogen or phosphoric acid. The reaction products of the phosphorous oxyhalogen over phosphoric acid are preferred. Such a reaction product is preferred for the continuous neutralization of alkali metal hydroxides in the equilibration of siloxanes.

24 Claims, No Drawings

SILYL PHOSPHATES AS NEUTRALIZING AGENTS FOR ALKALI METAL HYDROXIDES

BACKGROUND OF THE INVENTION

The present invention relates to silyl phosphates and more specifically the present invention relates to silyl phosphates which are useful as improved neutralizing agents for alkali metal hydroxides in siloxane equilibration reactions.

Heat vulcanizable silicone rubber compositions as well as room temperature vulcanizable silicone rubber compositions are well known. In the case of heat vulcanizable silicone rubber compositions, the basic ingredients comprises triorganosiloxy endstopped linear diorganopolysiloxane polymer having a viscosity of anywhere from 1,000,000 to 200,000,000 centipoise at 25° C. In the case of room temperature vulcanizable silicone rubber compositions the basic ingredient comprises a silanol endstopped linear diorganopolysiloxane polymer or a vinyl terminated linear diorganopolysiloxane having a viscosity of anywhere of 300 to 500,000 centipoise at 25° C. In the case of heat vulcanizable silicone rubber compositions, the triorganosiloxy endstopped diorganopolysiloxane polymer is usually prepared by equilibrating cyclic tetrasiloxanes in pure form at elevated temperatures, that is temperature above 100° C. in the presence of 5 to 500 parts per million of alkali metal hydroxide. The cyclic tetrasiloxanes that are utilized in such reactions are usually obtained by first hydrolyzing diorganodichlorosilanes in water and then cracking the hydrolyzate with an alkali metal hydroxide to obtain a mixture of cyclopolysiloxanes followed by a distillation to obtain the cyclic tetrasiloxanes.

In the above, the organo groups can be any monovalent hydrocarbon radical. In the case of the silanol endstopped diorganopolysiloxane polymers, such polymers are obtained by equilibrating cyclictetrasiloxanes or mixtures of cyclopolysiloxanes or a siloxane hydrolyzate at elevated temperatures, temperatures above 100° C., in the presence of small amounts of water or with small amounts of low molecular weight silanol endstopped diorganopolysiloxane polymers. The reaction is carried out in the presence of small amounts of alkali metal hydroxides until the desired viscosity polymer is obtained. In an alternate process, low viscosity silanol endstopped diorganopolysiloxane polymers are obtained by equilibrating pure cyclictetrasiloxanes or mixtures of polysiloxanes or siloxane hydrolyzates in the presence of acids such as toluenesulfonic acid or acid activated clay such as Filtrol sold by Filtrol Corporation of Los Angeles, California.

In the case of fluorosilicone polymers, such equilibration reactions can be carried out with facility with cyclictrisiloxanes in the presence of alkali metal hydroxides, most preferably sodium hydroxide. With such catalysts, there results the maximum production of linear polymer and also such catalysts belong to the class of the few catalysts that can be used in the production of high viscosity linear diorganopolysiloxane polymers. For the preparation of fluorosilicone polymers from cyclictetrasiloxanes, see for instance Razzano U.S. Pat. No. 3,997,496 and U.S. Pat. No. 3,937,684.

Going further into the equilibration reaction of cyclictrisiloxanes with the alkali metal hydroxides when approximately 85% (which is the maximum that can be converted of the cyclictetrasiloxane to the polymer) of the cyclictetrasiloxanes have converted to the polymer the catalyst is neutralized with an acidic material and the excess cyclics are distilled off to yield the desired linear diorganopolysiloxane polymer which can be utilized as a basic ingredient either in the heat vulcanizable silicone rubber compositions or in room temperature vulcanizable silicone rubber compositions depending on the viscosity of the polymer and whether it is silanol terminated or not.

Over the years various neutralizing agents have been tried for such alkali metal hydroxides, and alkali metal silanolates catalysts that are present in the equilibration mixture, after the equilibration has been reached. Such acids as hydrochloric, acetic, phosphoric and toluenesulfonic acid as well as other acids have been tried for neutralization of the alkali metal hydroxide catalyst. All of these neutralizing agents work with varying success. For instance, phosphoric acid is highly desirable in that it is a triprotic acid, which, when it is used in neutralizing an alkali metal hydroxide forms potassium dihydrophosphate, dipotassium hydrophosphate and tripotassium phosphate. The advantage of phosphoric acid is that the potassium dihydrophosphate and dipotassium hydrophosphate act as buffering agents in the system, which helps to protect the polymer from traces of acidic or basic impurities and is tolerant of small errors in adding the theoretical amount of phosphoric acid neutralizing agent. In the case of the other types of acidic neutralizing agents such as for instance toluenesulphonic acid, it was necessary to determine the exact amount of acid needed to neutralize the alkali metal hydroxide such that there would not be large residual amounts of acid left in the system which would degrade the linear polymer and finally the product in which it was incorporated. Accordingly, in such neutralization procedures, it was common to add the exact amount of acid and test the mixture for its pH and adjust the alkali metal hydroxide content or acid content to as close as neutral as was possible within the time limits of manufacturing production.

Accordingly, since phosphoric acid was a triprotic acid, it was highly preferred as a neutralizing agent for alkali metal hydroxides in the equilibration of siloxanes. However, phosphoric acid has one disadvantage, it is insoluble in siloxanes and as such would require constant agitation for long periods of time to obtain the proper mixing of the acid into the equilibration siloxane mixture. In a 50 gallon reaction kettle having therein a moderate viscosity siloxane mixture, it requires with moderate agitation 20 minutes for the phosphoric acid to blend into the siloxane mixture for neutralization purposes and with good agitation it requires 8 minutes. Accordingly, it should be noted that with the high viscosity high volume diorganopolysiloxane mixtures it would require excessive time for the blending of the phosphoric acid in this diorganopolysiloxane mixture.

It should also be noted that there are other triprotic acids such as for instance arsenic acid. However, this material is highly toxic as compared to the relatively non-toxic phosphoric acid, and also arsenic acid has undesirable reduction and oxidizing properties.

Accordingly, for one reason or another other triprotic acids have one disadvantage or another. As stated previously, phosphoric acid is readily available at low cost, is relatively non-toxic and has the desired buffering action in the neutralization of alkali metal hydroxides. There has also been developed a continuous process for the production of silanol endstopped diorganopolysiloxane polymers. Accordingly, phosphoric acid appears to be highly desirable as a continuous neutralizing agent for such continuous equilibration reactions. However, as stated previously, phosphoric acid has the disadvantage in that it is considerably insoluble in such siloxanes, and as such cannot be used in such continuous equilibration reactions since it would not blend into the siloxane equilibration mixture in the time allotted to carry out the desired neutralization and require complex mixing equipment. Accordingly, it was highly desirable to find a soluble form of phosphoric acid which would be utilized for the continuous equilibration neutralization of siloxane mixtures containing alkali metal hydroxides.

In the past few years there has been developed a soluble phosphate which is soluble in a siloxane mixture by reacting phosphoric acid and octylmethylcyclictetrasiloxanes with small amounts of chainstopper such as hexamethyldisiloxane. The resulting silyl phosphate had good neutralizing properties for siloxane equilibration reaction mixtures. However, such a material had two disadvantages, the most important disadvantage being that the viscosity of the silyl phosphate was above 500 centipoise at 25° C. making it difficult to blend into the siloxane equilibration reaction mixture. A minor disadvantage is that in the production of such silyl phosphates there could only be obtained silyl phosphates which had a phosphoric acid content at a maximum of 10 to 15% by weight. Accordingly, if there was desired to obtain a silyl phosphate with a higher phosphoric acid content it was not possible to obtain such a product using the prior art process. It was desired to obtain a silylphosphate having a phosphoric content of 20 to 30% by weight because such high phosphoric acid content silylphosphate would be desirable for fast neutralization of siloxane equilibration reaction mixture in continuous polymerization process.

Accordingly, it was highly desirable to have a process and a product that is a silyl phosphate which did not have the above disadvantages.

Accordingly, it is one object of the present invention to provide for a silyl phosphate which is obtained by reacting phosphorous oxyhalogen with a linear diorganosiloxane.

It is an additional object of the present invention to obtain a silyl phosphate which is obtained by reacting phosphoric acid with a linear diorganosiloxane.

It is an additional object of the present invention to provide for silyl phosphates which can have a phosphoric acid content of anywhere of 5 to 30% by weight and more preferably 20 to 30% by weight and a viscosity below 500 centipoise at 25° C.

It is still another object of the present invention to provide for a silyl phosphate which is imminently suitable in the continuous neutralization of alkali metal hydroxides in the continuous production of siloxanes.

It is still another object of the present invention to provide for a process for producing novel silyl phosphates, that generally can have a phosphoric acid content of anywhere from 5 to 30% by weight and a viscosity less than 500 centipoise at 25° C. These and other objects of the present invention are accomplished by means of the disclosure set forth herein below.

SUMMARY OF THE INVENTION

In accordance with the above objects, there is provided by the present invention a silylphosphate which is an improved neutralizing agent for alkali metal hydroxides in silicone reactions comprising the reaction product of a siloxane selected from the class of siloxanes of the formula,

and siloxanes of the formula,

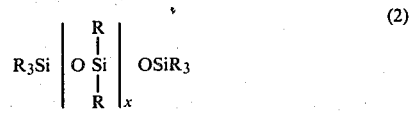

with phosphorous oxyhalogens selected from the class consisting of $PO\,Cl_3$ and $PO\,Br_3$ where R is a hydrocarbyl radical free of aliphatic unsaturation and x varies from 1 to 20. The above reaction product is obtained by reacting the foregoing phosphorous oxyhalogens and the diorganosiloxanes in which 3 moles of linear siloxane is used to react with one mole of the phosphorous oxyhalogen, to obtain a silylphosphate which may have a phosphoric acid content of as high as 30% by weight viscosity and having a viscosity substantially below 500 centipoise at 25° C. The process is carried out in the absence of solvents or catalysts at a temperature anywhere from 90° to 150° C. with the temperature generally being in the range of about 100° C. that is the reflux temperature of the linear siloxane of Formula 1. The reaction period takes anywhere from ½ to 3 hours. The phosphoric acid reacted with the linear siloxanes reaction product is less preferred since it is difficult to react the linear siloxanes of the foregoing formulas with a phosphoric acid, since the reaction with phosphoric acid takes place at a temperature of 150° C. and above. When phosphoric acid is utilized as the reactant, it is only necessary to react about 1 mole of phosphoric acid per 1½ moles of the linear siloxanes. Accordingly, the phosphoric acid process has the advantage of using up less of the linear siloxanes in forming the silylphosphate reaction product and in this respect the phosphoric acid reaction in accordance with the present invention is advantageous. As stated previously, both reactions can be carried out in the absence of catalysts and solvents unless the excess amounts of the linear siloxane that may be utilized is considered a solvent. Such amounts of the siloxane are not necessary. After the reaction is completed, the by-products which in the case of the phosphoric acid reaction is water while in the case of the phosphorous oxyhalogen is halosilanes, such by-products are simply distilled off to yield the desired silyl phosphate neutralizing agent. The acidity of the silylphosphate neutralizing agent may be then determined.

Most preferably the silylphosphate of the instant case is preferred as continuous neutralizing agent for continuous polymerization processes for forming diorganopolysiloxane polymers.

DESCRIPTION OF THE PREFERRED EMBODIMENT

The R radical in the linear siloxane of Formulas (1) and (2) can be selected from any monovalent hydrocarbon radical free of aliphatic unsaturation. It is preferred that there not be an aliphatically unsaturated radical in the linear siloxane in Formulas (1) and (2). Since any acid that is given up during the formation reaction when using phosphorous oxyhalide may add on to the unsaturated aliphatic radical of the silyl phosphate, it is most preferred that the siloxanes of Formulas (1) and (2) that the R radical not have aliphatic unsaturation. The R radical may be taken from monovalent hydrocarbon radicals such as alkyl radicals of from 1 to 8 carbon atoms such as methyl, ethyl, propyl, etc. cycloalkyl radicals such as cyclohexyl, cycloheptyl; mononuclear aryl radicals such as phenyl, methylphenyl, ethylphenyl, etc. It is also preferred that the R radicals not be a halogenated monovalent hydrocarbon radical, since during the neutralization process when the silyl phosphate is added to the equilibration siloxane mixture, the halogen may be given up to react with the alkali metal hydroxide to form an alkali metal salt such as potassium chloride. Such halogenated alkali metal salt such as potassium chloride degrade buffering action of the silyl phosphates of the instant case.

To form the neutralizing agents with the phosphorous oxy trichloride and phosphorous oxy tribromide are preferably reacted in stoichiometric amounts with linear siloxanes of Formulas (1) and (2) or with mixtures thereof such that there is reacted 3 moles of the linear siloxanes of Formulas (1) and (2) per 1 mole of the phosphorous oxytrichloride or phosphorousoxytribromide, so as to substitute the three halogen groups with a $R_3SiO$ unit or a

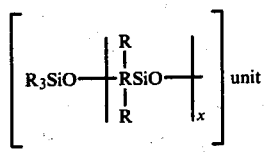

where x varies from 1 to 20. It should be noted that generally the x varies from 1 to 20 in the siloxane of Formula (2) and most preferably x varies from 1 to 10. The reason for this is that it is preferred to utilize as low a viscosity linear siloxane of Formula (2) as possible to produce the silyl phosphate reaction product since this will produce a low viscosity silyl phosphate, which is desired in the neutralization reactions of the instant case. The disiloxanes of Formula (1) may have a viscosity that is anywhere below 5 centipoise at 25° C. The linear siloxanes of Formula (2) have a viscosity of anywhere of up to 20 centipoise at 25° C. and more preferably when x is at value of 10 have a viscosity up to 10 centipoise at 25° C. Preferably in the above formulas R is an alkali radical of 1 to 8 carbon atoms and more preferably methyl. In the reaction that is carried out, it is preferred that no solvents be utilized. Solvents can be utilized but serve no purpose. Examples of solvents that can be utilized are for instance aromatic hydrocarbon solvents such as toluene, xylene, benzene, etc. If a solvent is desired for some purpose, as stated previously, excess amounts of the linear siloxanes of Formulas (1) and (2) can be utilized as solvents. In addition, it is not desired to utilize a catalyst since upon reaching a temperature of 100° C. the reactants will immediately react. Preferably the reaction is carried out at a temperature anywhere from 90° to 150° C. and more preferably from 90° to 130° C. More specifically, the reaction temperature can be determined by the reflux rate of the linear siloxane of Formulas (1) and (2) that are utilized as a reactant or by the reflux of the halosilane formed as a by-product of such a reaction. Generally, the linear siloxane or disiloxane of Formula (1) has a boiling point about 100° C. at atmospheric pressure when R is methyl and as such the reaction for this reactant would be carried out at that temperature or slightly less such in the neighborhood of 90° C.

In the case of the linear siloxane of Formula (2), if the reaction does not proceed at a sufficient rate at the temperatures of 100° to 125° C. to 130° C. then slightly higher temperatures may be utilized. Either with linear siloxanes of Formulas (1) and (2), a catalyst is not necessary since the reaction will proceed at a sufficiently fast rate without the use of the catalyst. As stated previously, additional amounts of excess amounts above 3 moles of the linear siloxanes of Formulas (1) and (2) may be utilized as reactants in the instant case so as to act as solvent for the silyl phosphate that is formed, but such is not necessary since the silyl phosphate product is a liquid. However, it is desirable that a 10% excess of the siloxanes of the Formulas (1) and (2) or mixtures thereof be utilized as a reactant since that insures the complete reaction of the phosphorous oxyhalogen compound. It should be noted that it is preferred that the preferred linear siloxane reactant is the one in Formula (1) since that results in a silyl phosphate with the highest equivalent content of phosphoric acid; that is, a phosphoric acid content of up to 30%. However, utilizing the linear siloxane of Formula (2) as a reactant, there may be obtained a silyl phosphate with an equivalent phosphoric acid content of anywhere from 5 to 25% by weight. Therefore, in accordance with the instant process there is obtained a silyl phosphate which has a phosphoric acid content which varies anywhere from 5 to 30% by weight and preferably from 20 to 30% by weight and a viscosity that is less than 500 centipoise at 25° C. It should also be noted that the reaction period of the present process with the phosphorous oxyhalogen compounds is short. The reaction takes place in a period of time anywhere from ½ to three hours and more preferably from anywhere from ½ to 1 hour with complete reaction taking place. The undesired by-products can be continuously removed from the reaction mixture by distillation. Thus by continually refluxing the reaction mixture to produce a silyl phosphate of the instant case, there can continually be removed during the reaction period, in the case of where the reactant is the phosphorous oxychloride or phosphorous oxy bromide, diorganodihalosilanes and triorganohalosilanes. These by-products are removed from the reaction mixture and later recycled to be utilized in the initial hydrolysis reactions for producing cyclicpolysiloxanes or disiloxanes and for other purposes. If such halo silane reaction products are not recycled, then there will be a loss of the desired silanes as a result of the production of the silyl phosphates in accordance with the above process. In this eventuality there is preferred that the phosphoric acid process for producing the silyl phosphates of the instant case. Utilizing the linear siloxane of Formula (1) and reacting with phosphorous oxy chloride or phosphorous oxy bromide there is obtained a product having the following formula: $(R_3SiO)_3P=O$ It should be noted that most of the product will have the above formula; however, there might be a minor amount condensed silyl substituted phosphates.

In the case the linear siloxane of Formula (2) is reacted with a phosphorous oxy chloride or phosphorous oxy bromide, then there is obtained a product of the formula,

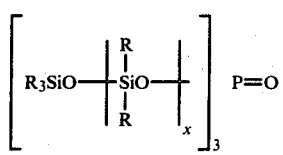

where x in the above formula is as previously defined. Again the by-products of the reaction of the linear siloxane of Formula (2) and the phosphorous oxy chloride or phosphorous oxy bromide that will be distilled overhead as a by-product are diorganodihalosilanes and triorganohalosilanes with the halogen group being either bromine or chlorine.

It should be noted that when it is desired to react a reaction mixture of the linear siloxanes of Formulas (1) and (2) with the phosphorous oxy bromide and phosphorous oxy chloride, that the product that is obtained will be a mixture of the compound of the above silyl phosphate formula and the reaction product will have a viscosity in accordance with the present invention which will be less than 500 centipoise at 25° C. viscosity. It should also be noted that with linear siloxanes of Formula (2) as a reactant that most of the product that is obtained will have the silyl phosphate formula as set forth above. However, there may be some monosilyl and disilyl substituted phosphates. However, these again will be in minimal quantities since the reaction has a great tendency to proceed to completion to form the silyl phosphates of the above formulas. Using the above reactions which are preferred in the instant case and utilizing preferably the linear siloxane or disiloxane of Formula (1) there may be obtained silyl phosphate having up to as much as 30% by weight or being equivalent to as much as 30% by weight of phosphoric acid.

It should be noted that with the preferred reactants of the above disclosure, that is specifically the phosphorous oxyhalogen compounds that the desired product is obtained in high yield.

The above reaction may also be carried out with phosphoric acid in place of phosphorous oxyhalogen compounds. However, such a reaction is carried out with difficulty. The reason for the difficulty is that the reaction with the phosphoric acid with the linear siloxanes of Formulas (1) or (2) does not take place readily unless temperatures of 150° to 200° C. and more preferably temperatures of 150° to 175° C. are utilized to carry out the reaction. The advantage of carrying out the reaction with phosphoric acid is that there is not given off as a by-product a halosilane which if not recycled would result in a loss in the process. If it is desired to make the maximum use of the linear siloxane of Formulas (1) and (2) without recycling chlorosilanes, then it is desirable to produce the silyl phosphate of the instant case utilizing phosphoric acid as a reactant in place of the phosphorous oxy chloride or the phosphorous oxy bromide reactants. In such a reaction 1 mole of phosphoric acid is reacted with 1½ moles or more of the linear siloxanes or more of Formulas (1) or (2) or mixtures there of. Accordingly, generally, there may be utilized from 1½ moles of the linear siloxanes of Formulas (1) or (2) with per mole of the phosphoric acid. If it is desired to have a certain amount of the linear siloxanes of Formulas (1) and (2) as a solvent then there may be utilized anywhere from 1½ moles to 6 moles of the linear siloxanes of Formulas (1) or (2) per mole of the phosphoric acid. If it is only desired to have a slight excess of the linear siloxanes of Formulas (1) and (2) and since the reaction is carried out with difficulty and so as to maximize the yield of the desired product, then preferably there is utilized anywhere from 1½ to 6 moles of the linear siloxanes of Formulas (1) and (2) per mole of phosphoric acid. If it is desired to utilize a solvent, any of the common hydrocarbon solvents may be utilized and more preferably aromatic hydrocarbon solvents such as xylene, toluene, etc.

Accordingly, in the second process, the process is carried out with the reactants at a temperature of 150° to 200° C. and more preferably at 150° to 175° C. distilling water off as a by-product until the reaction is completed and may be terminated. In this second reaction, the reaction does not proceed as readily as the first, and accordingly a reaction time of anywhere from 1 to 7 hours is necessary and more preferably a reaction time of from 1 to 4 hours may be necessary. Again utilizing the linear siloxane of Formula (1), which is reacted with phosphoric acid there is obtained a silyl phosphate of the formula [R₃ Si O]₃ P=O and utilizing the linear siloxanes of Formula (2) and reacted with phosphoric acid that is obtained in silyl phosphate of the formula,

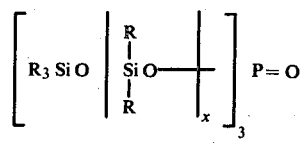

It should be noted that with respect to the silyl phosphates obtained by reacting the linear siloxanes of Formula (1), that since the reaction is carried out with more difficulty and may not proceed to completion there may be some amounts of monosilyl and disilyl substituted phosphate reaction products. In that case the phosphoric acid will be left with one or two hydroxy groups. The above is also true when the linear siloxane of Formula (2) is reacted with phosphoric acid since this reaction proceeds also with difficulty such that there may be some amounts of the monosilyl and disilyl phosphate substituted reaction product. In both cases the monosilyl and disilyl substituted reaction products may constitute as much as 10% by weight and preferably not more than 5% by weight of the total reaction product. It is, of course, obvious that if a mixture of linear siloxane of Formula (1) and Formula (2) are utilized in the reaction mixture there will be obtained reaction product mixtures of the completely substituted silyl phosphates of the above formulas and a mixture of appropriate monosilyl and disilyl substituted phosphate. The reaction mixture may be simply heated at atmospheric pressures to the boiling point of the reactants and thus the water may be removed by azeotroping with the siloxane. Thus, in this reaction with phosphoric acid there will be a small amount of various phosphorous compounds that may be formed. This is especially so when the linear siloxane of Formula (2) is utilized as reactant. Thus, there may be formed for instance some minor amounts of diorganopolysiloxanes chainstopped with —P=O radicals. The silyl phosphate reaction product consisting mostly of trisilyl substituted phosphates is then ready to be utilized to neutralize the equilibration siloxane reaction mixtures having therein alkali metal hydroxide compounds. Utilizing the phosphoric acid process which is advantageous in that no halogenated by-products are given off there may be obtained a silyl phosphate product having a viscosity of less than 500 centipoise at 25° C. and more preferably having a viscosity less than 200 centipoise at 25° C. The phosphoric acid content of the silyl phosphate may vary anywhere from 5 to 30% by weight and more preferably varies from 10 to 30% by weight. It is noted that when the linear siloxanes of Formula (1) is utilized solely in the reaction of the phosphoric acid and in accordance with the instant disclosure then there will be obtained a silyl phosphate reaction product which will have a phosphoric acid content that will vary anywhere from 20 to 30% by weight with a minor amount of monosilyl and disilyl substituted phosphates. The foregoing limitations and definitions set forth with respect to the linear siloxanes of Formulas (1) and (2) with respect to the reaction of the linear siloxanes with the phosphorous oxyhalogen compound also apply to the reaction of the linear siloxanes of Formulas (1) and (2) in the phosphoric acid process.

It should be noted that a silyl phosphate reaction product can be produced in accordance with the instant invention with the phosphoric acid content is less than 5% by weight, however, for convenience sake the use of such low acid equivalent silyl phosphate would not be desired since it would take a large amount of it to neutralize an equilibration siloxane reaction mixture. In addition, it is possible to produce silyl phosphate of somewhat about 30% by weight of phosphoric acid content, however, such a silyl phosphate would be only a few percentage points above 30% so as to obtain the maximum content possible in which the care necessary to get the maximum level detracts in carrying out such a process. However, if it was desired and utilizing the linear siloxane of Formula (1), such a silyl phosphate of maximum phosphoric acid content could be produced in accordance with the process of the instant case and specifically with the phosphorous oxy chloride and phosphorous oxy bromide reactants.

It should be noted that because the linear siloxane of Formula (2) has more siloxane groups in it than the disiloxane there is obtained more silyl phosphate reaction products in which the acid content is further diluted by siloxane groups in the reaction product. It is desired to utilize the linear siloxane of Formula (2) as reacted with phosphorous oxy chloride or phosphorous oxy bromide compounds or the phosphoric acid when it is not desired to obtain a silyl phosphate reaction product of the higher phosphoric acid content, that is a phosphoric acid content in the are of 5 to 25% or preferably 5 to 20%. Particularly, the linear siloxane of Formulas (1) and (2) that is utilized to obtain a specific silyl phosphate will of course depend on the demands of the neutralization process in which the reaction product is to be utilized. Of course, it should be noted that the silyl phosphates obtained by the reaction of the linear siloxanes of Formula (2) have a higher silicone content and as such the silyl phosphate that are formed are more compatible and more soluble in most siloxane equilibration reaction mixtures and as such, in certain instances they may be preferred. On the other hand, the silyl phosphate reaction products obtained with the linear siloxane of Formula (1) have a high phosphoric acid content and have a suitable solubility in many siloxane equilibration mixtures and are thus desired in neutralization reactions where very rapid neutralization is desired. Such a neutralization is for instance desired in continuous polymerization processes.

Such a continuous polymerization process for instance can comprise continuously equilibrated a stream of polydimethylcyclicsiloxanes in the presence of small quantities of low molecular weight silanol endstopped diorganopolysiloxane polymer or water to which is continuously added a catalytic amount of alkali metal hydroxide. By the time the flowing stream of cyclicpolysiloxanes has been passed through the equilibration zone continuously moving at a temperature of anywhere from 100° to 200° C. and when it was reached the end of the polymerization column most of the cyclic siloxanes have been converted to linear diorganopolysiloxane polymer chainstopped with silanols and alkali metal silanolates. The stream is then continuously moved to a static mixer wherein the static mixer there is continuously added to the stream an appropriate amount of a silyl phosphate neutralizing agent of the present invention. By the time the siloxane equilibration stream has reached the end of the static mixer, the siloxane reaction mixture is completely neutralized, which time period can be in the neighborhood of 5 minutes or less. The volatiles may then be continually vented off from the neutralized silanol endstopped diorganopolysiloxane polymer that has been formed to yield the desired silanol endstopped diorganopolysiloxane polymer useful in forming the basic ingredient for room temperature vulcanizable silicone rubber compositions. It is recognized that the procedures and the apparatuses may vary in such continuous polymerizations of linear diorganopolysiloxane polymers, the above procedure that was given being exemplary. At any rate, the silyl phosphate of the instant invention are extremely suitable as continuous neutralizing agents in a continuous polymerization reaction of organopolysiloxanes. It should be noted that the silyl phosphates of the instant case are advantageous for neutralization reactions of any silicone polymer whether the process is continuous or batch.

However, the silyl phosphates of the instant case because of their rapid neutralization of alkali metal hydroxides in silicone mixtures are especially suitable for continuous neutralization of alkali metal hydroxide in the continuous process for the preparation of silicone polymers.

The Examples below are given for the purpose of illustrating the present invention. They are not given for any purpose in setting the limits in defining the extent of the invention of the instant case. All parts are by weight.

EXAMPLE 1

A one liter, 3 neck flask was set up containing a magnetic stirrer and a short reflux column with condensor, thermometer, and receiver. 567 grams (3.5 moles) of hexamethyldisiloxane and 152.5 grams (one mole) of phosphorous oxychloride was added. The contents of the flask were constantly agitated and heat was applied. The flask was brought to reflux and the column was maintained at total reflux. Within 30 minutes the column head temperature was at 58°, indicating formation of trimethyl chlorosilane. At this point, take off was begun at about a 4 to 1 reflux ratio. Within 2 hours a substantial quantity of chlorosilane had been collected and the head temperature began to rise. Distillate continued to be collected until the head temperature reached 100° C., the boiling point of hexamethyl disiloxane. Distillation was continued until the head temperature began to drop. The total amount of distillate was 387 grams. There remained 329 g. of residue. The total chloride content of the residue (by sodium biphenyl digestion) was less than 100 ppm. A sample of the silylphosphate residue was added to hot distilled water and agitated for 30 minutes. The solution was titrated with 0.1 N aqueous potassium hydroxide. The phosphoric acid equivalence of the residue silyl phosphate was 30.9%.

EXAMPLE 2

A one liter flask was equipped with a mechanical stirrer, thermometer, and a condensor with a Dean-Stark Trap. 620 g (2 moles) of decamethyltetrasiloxane and 88 grams of 85% phosphoric acid were added to the flask and the immiscible contents were heated under moderate agitation. At 170° C. some water began to be evolved and collected in the trap. The temperature was raised to 180° C. and a substantial amount of water began to be collected. The agitation rate was increased due to some frothing in the flask. Small amounts of additional water were collected over the next 2.5 hours until the theoretical amount of water (20.5 grams) was collected. Approximately 15 ml of siloxanes were also lost in the trap. The residue (670 g) was cooled and a sample was added to hot distilled water and shaken for 20 minutes. An aliquot was taken and titrated with aqueous A.1N KOH solution. The silyl phosphate residue was found to have a phosphoric acid equivalence of 12.5%.

We claim:

1. A silyl phosphate which is an improved neutralizing agent for alkali metal hydroxides in silicone reactions comprising the reaction product of a siloxane selected from the class consisting of siloxanes of the formula,

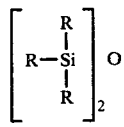

and siloxane of the formula,

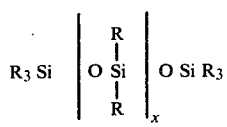

with a halophosphorous compound selected from the class consisting of PO Cl$_3$ and PO Br$_3$ where R is a hydrocarbyl radical free of aliphatic unsaturation and x varies from 1 to 20.

2. The reaction product of claim 1 wherein there is present 3 moles of the siloxane per mole of the halophosphorous compound.

3. The reaction product of claim 1 which has the formula, (R$_3$ SiO)$_3$ P=O

4. The reaction product of claim 1 which has the formula,

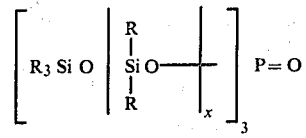

5. The reaction product of claim 1 wherein R is an alkyl radical of 1 to 8 carbon atoms.

6. The reaction product of claim 1 wherein R is methyl and the reaction product has phosphoric acid content that varies from 5 to 30% by weight.

7. A process for forming a silyl phosphate which is an improved neutralizing agent from alkali metal hydroxide in silicone mixture comprising, (a) reacting a siloxane selected from the class consisting of siloxanes of the formula,

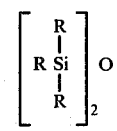

and siloxanes of the formula,

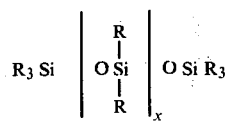

with a halophosphorous compound selected from the class consisting of PO Cl$_3$ and PO Br$_3$ wherein R is hydrocarbyl radical free of aliphatic unsaturation and x varies from 1 to 20 and (b) distilling off undesired by-products.

8. The process of claim 7 wherein in step (a) there is reacted 3 moles of the siloxane per mole of the halophosphorous compound.

9. The process of claim 7 wherein the reaction is carried out at temperatures in the range of 80° to 150° C.

10. The process of claim 1 wherein R is an alkyl radical of 1 to 8 carbon atoms.

11. The process of claim 1 wherein R is methyl and the product of the reaction has a phosphoric acid content that varies from 5 to 30% by weight and a viscosity that is less than 500 centipoise at 25° C.

12. A silyl phosphate which is an improved neutralizing agent for alkali metal hydroxides in the silicone reactions comprising the reaction product of a siloxane selected from the class consisting of siloxanes of the formula,

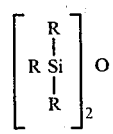

and siloxanes of the formula,

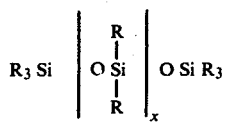

with phosphoric acid, where R is a hydrocarbyl radical free of aliphatic concentration and x varies from 1 to 20.

13. The reaction product of claim 12 wherein there is present 1.5 moles of the siloxane per mole of the phosphoric acid.

14. The reaction product of claim 12, wherein a major portion of the product has the formula,

[R$_3$ Si O]$_3$ P=O

15. The reaction product of claim 12, wherein a major portion of the product has the formula,

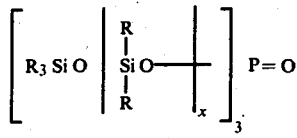

16. The reaction product of claim 12 wherein R is an alkyl radical of 1 to 8 carbon atoms.

17. The reaction product of claim 12 wherein R is methyl and the reaction product has a phosphoric acid content that varies from 5 to 30% by weight.

18. A process for forming a silyl phosphate which is an improved neutralizing agent for alkali metal hydroxides in silicone reactions comprising (a) reacting a siloxane selected from the class consisting of siloxanes of the formula,

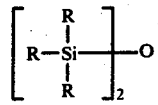

and siloxanes of the formula,

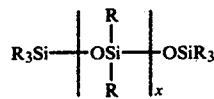

with phosphoric acid wherein R is a hydrocarbyl radical free of aliphatic concentration and x varies from 1 to 20 and (b) distilling of H$_2$O.

19. The process of claim 18 wherein in step (a) there is reacted 1.5 moles of the siloxanes per mole of the phosphoric acid.

20. The process of claim 18 wherein the reaction is carried out at a temperature of 150°–195° C.

21. The process of claim 18 where R is an alkyl radical of 1 to 8 carbon atoms.

22. The process of claim 18 wherein R is methyl and the product of the reaction has phosphoric acid content that varies from 5 to 30% by weight and a viscosity that is less than 500 centipoise at 25° C.

23. A process of continuously neutralizing basic alkali metal silicone compounds present in siloxane equilibration reacting products comprising continuously adding to said siloxane equilibration reaction products a neutralizing amount of the reaction product of a siloxane selected from the class consisting of siloxanes of the formula,

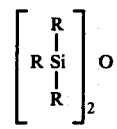

with a halophosphorous compound selected from the class consisting of PO Cl$_3$ and PO Br$_3$ where R is a hydrocarbyl radical free of aliphatic unsaturation and x varies from 1 to 20.

24. A process for continuously neutralizing basic aliphatic metal silicone compounds present in siloxane equilibration reaction products comprising continuously adding to said siloxane equilibration reaction products a neutralizing amount of the reaction product of a siloxane selected from the class consisting of siloxanes of the formula,

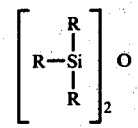

and siloxanes of the formula,

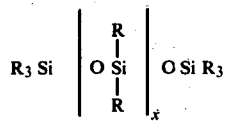

with phosphoric acid where R is a hydrocarbyl radical free of aliphatic unsaturation and x varies from 1 to 20.

* * * * *